(12) United States Patent (10) Patent No.: US 6,290,499 B1
Lazzara et al. (45) Date of Patent: Sep. 18, 2001

(54) TRANSFER-TYPE IMPRESSION COPING

(75) Inventors: Richard J. Lazzara, Lake Worth; Keith D. Beaty, Jupiter; Dan Paul Rogers, Royal Palm Beach, all of FL (US); Curtis E. Jansen, Pacific Grove, CA (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

(21) Appl. No.: 09/374,934

(22) Filed: Aug. 16, 1999

Related U.S. Application Data

(60) Division of application No. 08/967,147, filed on Nov. 10, 1997, now Pat. No. 5,938,443, which is a continuation-in-part of application No. 08/401,801, filed on Mar. 10, 1995, now Pat. No. 5,685,715, which is a continuation-in-part of application No. 08/337,387, filed on Nov. 8, 1994, now Pat. No. 5,899,695.

(51) Int. Cl.$^7$ .................................................. A61C 8/00
(52) U.S. Cl. ........................ 433/173; 433/172; 433/214
(58) Field of Search .................................... 433/172, 173, 433/174, 175, 176, 214

(56) References Cited

U.S. PATENT DOCUMENTS

| | | |
|---|---|---|
| 4,758,161 | 7/1988 | Niznick . |
| 4,850,870 | 7/1989 | Lazzara et al. . |
| 4,850,873 | 7/1989 | Lazzara et al. . |
| 4,854,872 | 8/1989 | Detsch ............................ 433/173 |
| 4,856,994 | 8/1989 | Lazzara et al. . |
| 4,955,811 | 9/1990 | Lazzara et al. . |
| 4,988,298 | 1/1991 | Lazzara et al. . |
| 5,006,069 | 4/1991 | Lazzara et al. . |
| 5,015,186 | 5/1991 | Detsch . |
| 5,030,096 | 7/1991 | Hurson et al. . |
| 5,035,619 | 7/1991 | Daftary . |

(List continued on next page.)

FOREIGN PATENT DOCUMENTS 0 657 146 A1  6/1995  (EP) .

OTHER PUBLICATIONS

Exhibit A, a drawing of a healing abutment.
Exhibit B, an assembly drawing of a coping and the component drawings which comprise the coping assembly.
Exhibit C, a one–piece healing abutment made entirely of DELRIN™.

(List continued on next page.)

*Primary Examiner*—Nicholas D. Lucchesi
(74) *Attorney, Agent, or Firm*—Jenkens & Gilchrist

(57) ABSTRACT

A set of dental impression components that may be used for either pick-up type (open tray) or transfer type (closed tray) impression molding techniques. The components are used with an impression material to fabricate a model at a site in a jawbone where an implant has been osseointegrated. The impression components include an impression coping having an outer surface with its bottom end configured to reside below the gingiva surrounding the implant. A passage exists through the impression coping which accepts a first means for attaching the impression coping to the implant for use in a pick-up type impression application. The passage also accepts a second means for attaching the impression coping to the implant for use in a transfer type impression application.

33 Claims, 6 Drawing Sheets

U.S. PATENT DOCUMENTS

| | | |
|---|---|---|
| 5,040,983 | 8/1991 | Binon . |
| 5,064,375 | 11/1991 | Jorneus ................................. 433/174 |
| 5,071,351 | 12/1991 | Green, Jr. et al. . |
| 5,073,111 | 12/1991 | Daftary . |
| 5,100,323 | 3/1992 | Friedman et al. . |
| 5,106,300 | 4/1992 | Voitik ................................... 433/173 |
| 5,125,841 * | 6/1992 | Carlsson et al. ................. 433/172 X |
| 5,135,395 | 8/1992 | Marlin . |
| 5,145,371 | 9/1992 | Jorneus . |
| 5,145,372 | 9/1992 | Daftary et al. . |
| 5,154,612 | 10/1992 | Carlsson et al. . |
| 5,188,800 | 2/1993 | Green, Jr. et al. . |
| 5,209,659 | 5/1993 | Friedman et al. . |
| 5,209,666 | 5/1993 | Balfour et al. . |
| 5,213,502 | 5/1993 | Daftary ................................. 433/214 |
| 5,238,405 * | 8/1993 | Marlin ................................... 433/173 |
| 5,246,370 | 9/1993 | Coatoam . |
| 5,281,140 | 1/1994 | Niznick . |
| 5,292,252 | 3/1994 | Nickerson et al. . |
| 5,297,963 | 3/1994 | Daftary . |
| 5,312,254 | 5/1994 | Rosenlicht . |
| 5,316,476 | 5/1994 | Krauser . |
| 5,334,024 | 8/1994 | Niznick ................................. 433/172 |
| 5,336,090 | 8/1994 | Wilson, Jr. et al. . |
| 5,338,196 | 8/1994 | Beaty et al. . |
| 5,368,483 | 11/1994 | Sutter et al. . |
| 5,419,702 | 5/1995 | Beaty et al. . |
| 5,431,567 | 7/1995 | Daftary . |
| 5,476,383 | 12/1995 | Beaty et al. . |
| 5,492,471 | 2/1996 | Singer . |
| 5,527,182 | 6/1996 | Willoughby ......................... 433/172 |
| 5,538,426 * | 7/1996 | Harding et al. ................. 433/173 X |
| 5,564,921 * | 10/1996 | Marlin ............................. 433/173 X |
| 5,651,675 | 7/1997 | Singer ................................... 433/172 |
| 5,662,476 * | 9/1997 | Ingber et al. ..................... 433/173 X |
| 5,674,069 | 10/1997 | Osorio ................................... 433/172 |
| 5,674,071 | 10/1997 | Beaty et al. ......................... 433/172 |
| 5,674,073 | 10/1997 | Ingber et al. ........................ 433/213 |
| 5,681,167 | 10/1997 | Lazarof ................................. 433/174 |
| 5,688,123 * | 11/1997 | Meiers et al. .................... 433/172 X |

OTHER PUBLICATIONS

Bränemark System, Product Catalog Prosthetics 1991, Nobelpharma (3 pages).

DIA™ Dental Imaging Associates, Inplamed—The Source, *The Anatomical Abutment System,* Copyright Date Oct. 9, 1991 on p. 10 (front cover, pp. 1–10, and back cover).

IMPLA–MED The Source, IMPLA–MED Prosthetic Components (11–1992) (3 pages).

Implant Support Systems, Inc., Catalog Summer 1993 (2 pages).

IMTEC Hexed–Head™ Implant System, IMTEC Prosthetic Components, Spring 1993 Catalog (2 pages).

Interpore International, Restorative Components, Price and Data Sheet, May, 1990 (2 pages).

Lewis et al., Single Tooth Implant Supported Restorations, *Intnatl. Jrnl. of Oral & Maxillofacial Implants,* vol. 3, No. 1, pp. 25–30, 1988.

Lewis et al., The "UCLA" Abutment, *Intnatl. Jrnl. of Oral & Maxillofacial Implants,* vol. 3, No. 3, pp. 183–189, 1988.

Perri, Geroge, DDS et al., Single Tooth Implants, *CDA Journal,* vol. 17, No. 3, Mar. 1989.

Prosthetic Catalog, 1993, Implant Innovations, Inc. (3 pages).

Prosthetic Catalog, Impression Copings, Implant Innovations, Inc. (3 pages).

Zarb, George A. and Thomas Jansson, Tissue–Integrated Prostheses, Osseointegration in Clinical Dentistry, Chapter 17, *Laboratory Procedures and Protocol,* pp. 293–315, 1985.

* cited by examiner

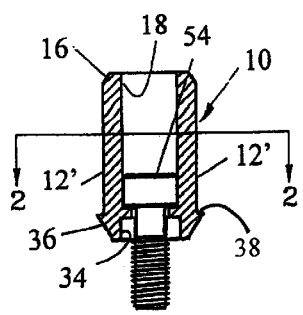
Fig. 1
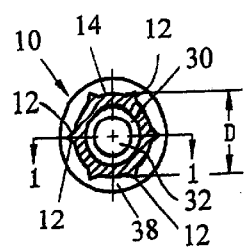
Fig. 2
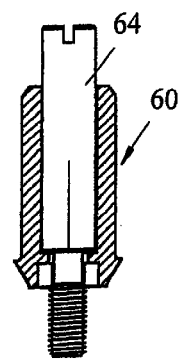
Fig. 6
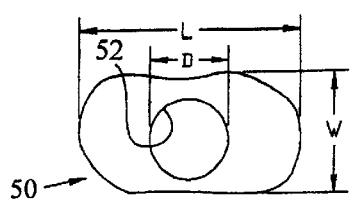
Fig. 4
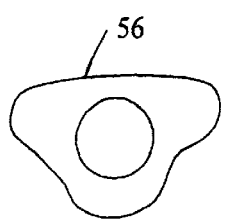
Fig. 5
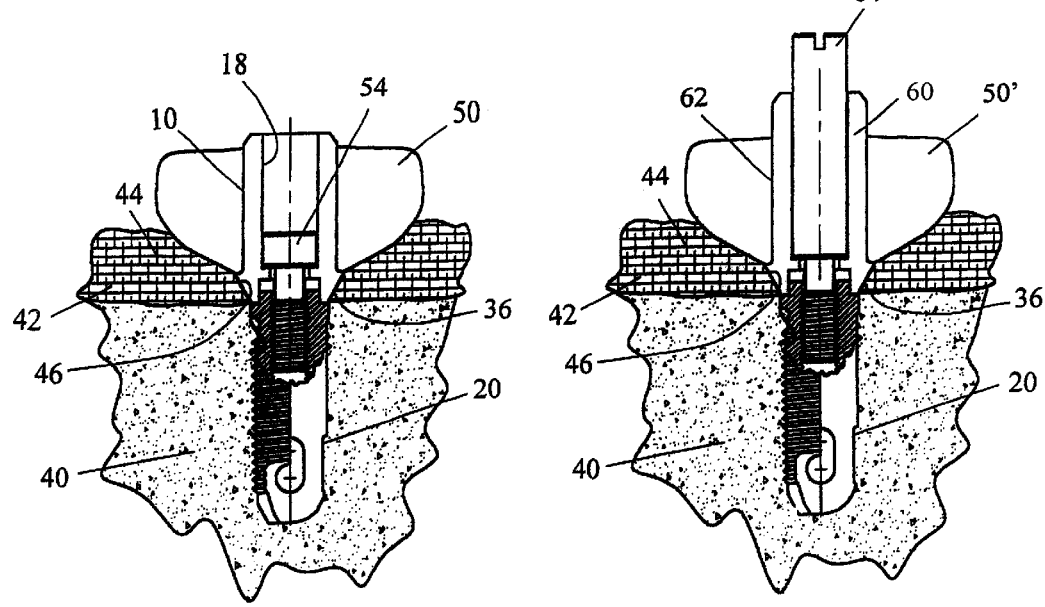
Fig. 3
Fig. 7

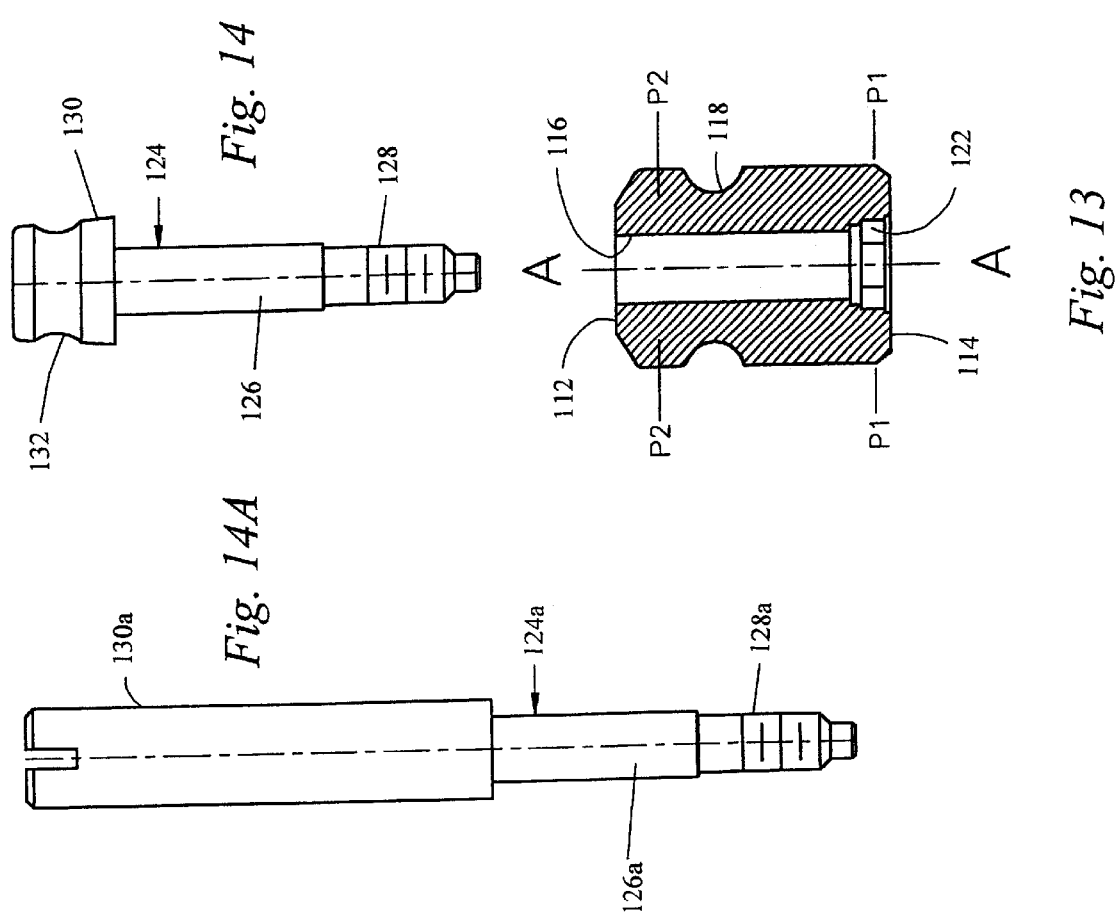

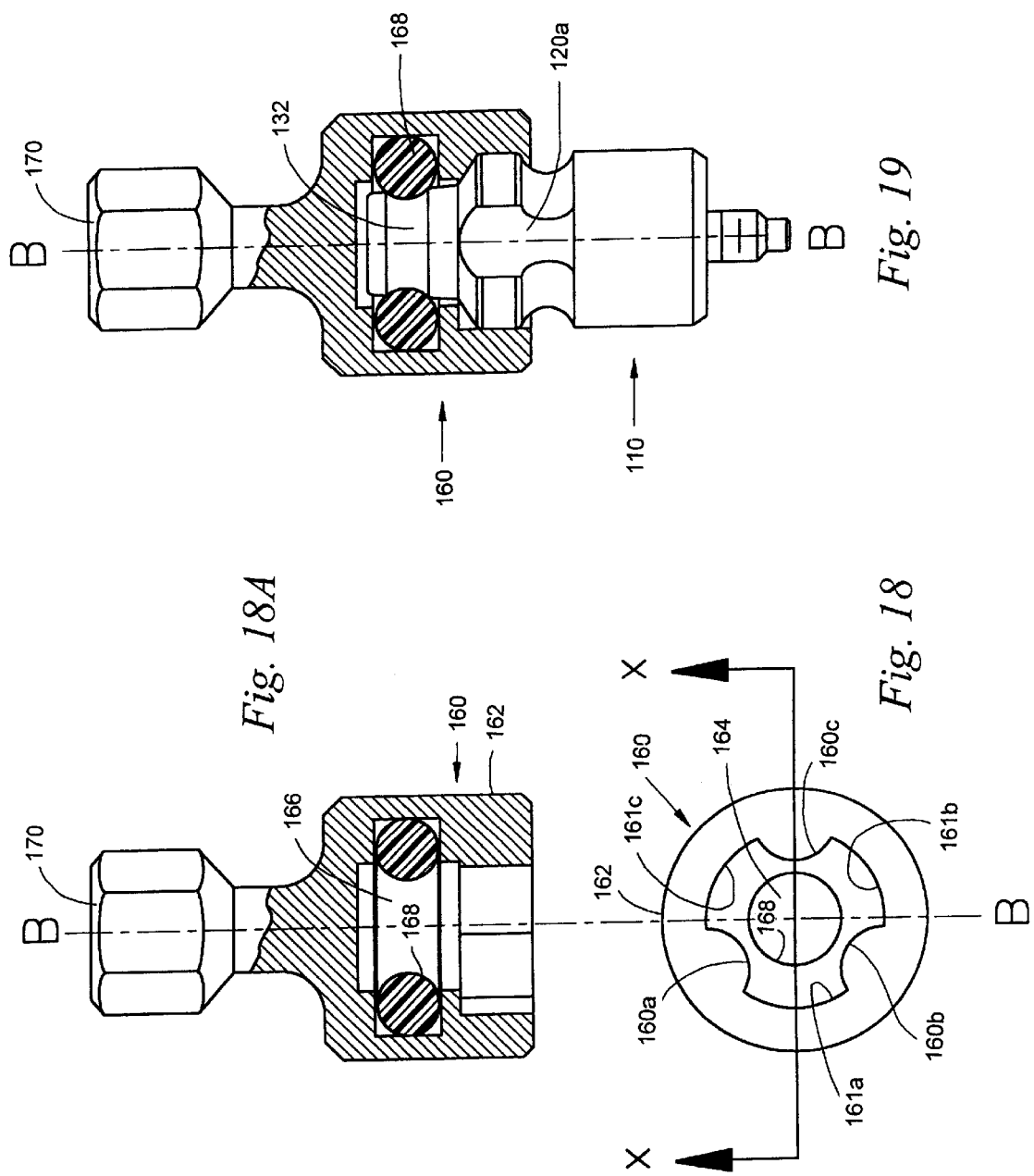

TRANSFER-TYPE IMPRESSION COPING

CROSS REFERENCES TO RELATED APPLICATIONS

This application is a divisional application of Ser. No. 08/967,147, filed on Nov. 10, 1997, now U.S. Pat. No. 5,938,443, issued on Aug. 17, 1999, which is a continuation-in-part Ser. No. 08/401,801, filed Mar. 10, 1995, now U.S. Pat. No. 5,685,715, issued on Nov. 11, 1997.

This application is a continuation-in-part claiming the benefit of copending patent applications Ser. No. 08/337,387, filed Nov. 8, 1994, now U.S. Pat. No. 5,899,695.

FIELD OF THE INVENTION

This invention relates to the dental implant industry. More specifically, this invention relates to impression copings for use as either a pick-up type or transfer type impression coping.

BACKGROUND OF THE INVENTION

For an artificial tooth (i.e. "dental restoration") to closely replicate the lost natural tooth that it replaces, the artificial tooth must emerge from the gum tissue with the same shape and contour as did the natural tooth. Currently, dental implants, which function as artificial tooth roots, are embedded in the bone tissue of the maxillary and mandible. After these implants have osseointegrated, it is necessary to form the gingiva overlying the bone where the implant is installed. Healing components function to expand a transmucosal opening from the round shape of the implant to a size that more nearly approximates the size of the tooth where it emerges from the gum. After the healing components form the gingival tissue, an impression component is used to make a model of the patients mouth in the area of the implant site.

Creating an artificial tooth for a patient who has been fitted with one or more dental implants begins with taking this impression of the patient's case. Dental implants have locking means (usually a hexagonal boss) useful to interlock with corresponding locking means in the components fitted to them when it is desired to prevent rotation of a component relative to the implant around the longitudinal axis of the implant. Once as implant has become osseointegrated with the host bone, it becomes necessary to preserve in the impression the information describing the orientation of its hex. Recording the correct hex orientation is critical if an accurate model of the patient's case is to be created in the dental laboratory. The component used to effect this information transfer is commonly called an "impression coping".

By its very nature the impression material is resilient and soft enough that it can be removed from the patient's mouth after it has set up, yet firm enough that it can preserve information imparted to it by an impression coping. If the coping used is a transfer type impression coping, it will remain in the patient's mouth when the impression material is removed, pulling the transfer coping out of the socket formed around it in the impression. This technique is known in the art as the "closed tray method". If the coping used is a pick-up type impression coping, it will remain within the impression when the material is removed from the patient's mouth. This technique is known in the art as the "open tray method."

A problem that exists with current impression components is that components used for pick-up type impression coping cannot be used for transfer type impression coping and vice versa. This forces manufacturers to produce two separate lines of impression coping components—one for pick-up type and one for transfer type. Moreover, clinicians are forced to maintain separate inventories of components to be used with either method.

Therefore, it is an object of the present invention to provide an impression coping component which may be interchangeably used with either pick-up type or transfer type impression coping methods.

SUMMARY OF THE INVENTION

The impression components of the present invention include the improved feature of accepting differently sized coping screws which are used to attach the coping component to the implant. By fastening the coping component to the implant with a longer coping screw, the coping component may be used as a pick-up type impression coping. However, the identical coping component may be used as a transfer type impression coping if a shorter coping screw is used. Therefore, the present invention allows one single coping component to be used for either pick-up type or transfer type impression coping by altering the coping screw used to secure the component to the implant.

This invention is described as a set of dental impression components that may be used for either pick-up type (open tray) or transfer type (closed tray) impression molding techniques. The components are used with an impression material to fabricate a model at a site in a jawbone where an implant has been osseointegrated. The impression components include an impression coping having an outer surface with its bottom end configured to reside below the gingiva surrounding the implant. A passage exists through the impression coping which accepts a first means for attaching the impression coping to the implant for use in a pick-up type impression application. The passage also accepts a second means for attaching the impression coping to the implant for use in a transfer type impression application.

Additional objects and features of the invention will be apparent in the following description of exemplary embodiments of the invention with reference to the accompanying drawings. The scope of the invention is delineated in the claims that are appended to this application.

BRIEF DESCRIPTION OF THE DRAWINGS

In the accompanying drawings:

FIG. 1 is a longitudinal section through a core abutment according to the invention;

FIG. 2 is a transverse section through FIG. 1;

FIG. 3 is a side view of an emergence profiler component assembled on a dental implant;

FIG. 4 is a top view of an emergence profiler component of the invention;

FIG. 5 is a top view of another emergence profiler component;

FIG. 6 is a longitudinal section through a core abutment for use as a pick-up type impression coping;

FIG. 7 is a side view of a pick-up type impression coping assembled on a dental implant;

FIG. 13 is a longitudinal section through FIG. 12;

FIG. 14 is a side view of a coping screw used for transfer type impression coping;

FIG. 14A is a side view of a coping screw used or pick-up type impression coping;

FIG. 15 is a side view of the coping and transfer type coping screw fitted together;

FIG. 15A schematically shows a typical implant in position for attaching the coping and coping screw to the implant;

FIG. 18 is an end view of a driving tool;

FIG. 18A is a longitudinal section on line X—X of FIG. 18; and

FIG. 19 shows the driving tool coupled to the coping of FIG. 15.

DETAILED DESCRIPTION OF THE DRAWINGS

Figures 8, 9:
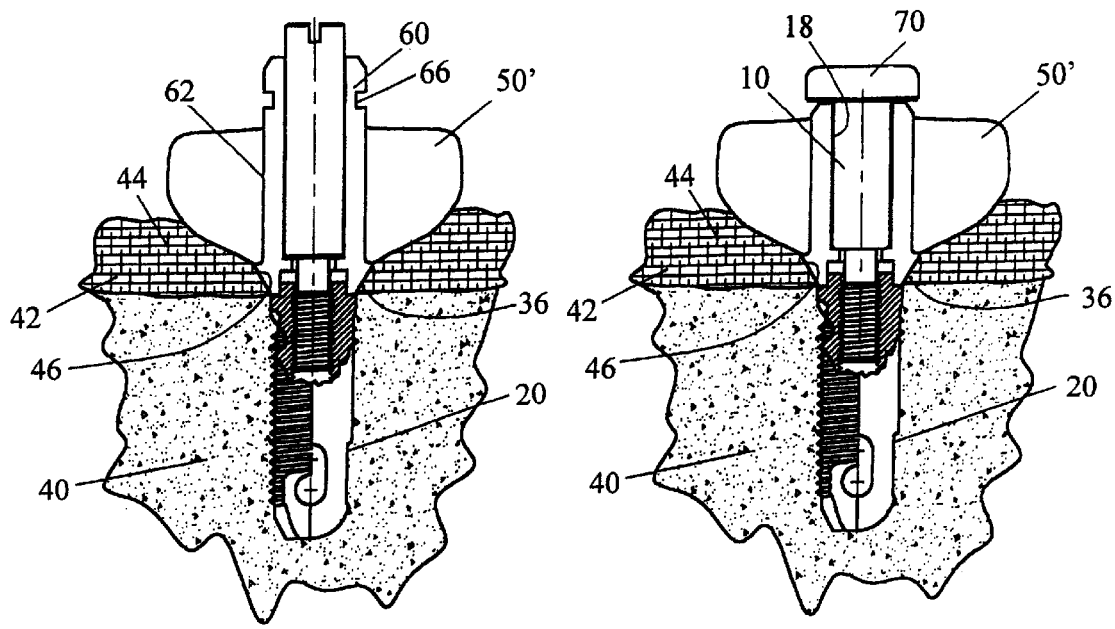
FIG. 8 is another embodiment of a pick-up type impression coping.
FIG. 9 shows a transfer type impression coping according to the invention.

Referring first to FIGS. 1 to 3, a core component 10 is generally tubular in form with an outer diameter "D" substantially the same as the diameter of the implant 20 (FIG. 3) on which it is to be mounted. Longitudinally-oriented ribs 12 are on the outer surface 14 which defines the diameter "D." Preferably, the ribs 12 have sharp edges 12', seen in FIG. 1. The ends 16 of the ribs at the supragingival end 18 of the core component are sloped toward the sharp edges. Six ribs are illustrated in FIG. 2, but the number of ribs can be different. In other structural respects illustrated in the drawings, the core component is similar to known abutments; that is, the transverse member 30 defining a screw hole 32 and the top surface of a hexagonal socket 34, and the expanded subgingival end 36 with its shoulder 38, are known features of existing abutments.

In FIG. 3 the core component 10 is shown installed on a dental implant 20 which is fixed in bone 40 having overlying gingiva 42 with an aperture 46 giving access to the implant. As is the prevailing dental practice, the implant is substantially entirely encased in the bone, and the subgingival end 36 is mated to the implant, through the aperture, within the gingiva, at the junction of the gingiva and the bone. The emergence profile to be given to the aperture 46 through the gingiva will depend on the type of tooth that was in the site where the implant is now installed. FIGS. 3 and 4 illustrate a molar-type emergence profiler abutment guide 50, for use as a healing component, having a mesial-distal dimension "L" and a buccal-labial dimension "W" which are characteristic of that type. A through-bore 52 through this emergence profiler 50 has the same diameter "D" as the core component 10. In use the emergence profiler 50 is forced over the core component 10 so that the ribs 12 become embedded in the walls of the through-bore 52 until the emergence profiler 50 is seated on the shoulder 38. The assembly of both components is then attached to the implant in known fashion, using an abutment screw 54. The core component 10 is thereby fixed non-rotatively on the implant 20, and the emergence profiler 50 is thereby fixed non-rotatively on the core component 10.

As is apparent in FIGS. 3 and 4, the emergence profiler 50 is now fixed in a position to force the aperture 46 to heal in a contour which closely replicates the emergence profile of a premolar-type tooth. FIG. 5 illustrates an alternative emergence profiler 56 that can be used for restoration of another type tooth. It will be apparent that pairs of such tooth-shaped components can be provided at low cost in a wide variety of shapes, contours and sizes for a wide variety of tooth types.

Referring now to FIGS. 6 and 7, the invention is illustrated as it may be used to take an impression preparatory to making a laboratory model. A core abutment 60 intended for use as a pick-up type impression coping is longer than the core abutment 10, and a pick-up type coping screw 64 replaces the abutment screw 54. Otherwise the two core abutments are substantially identical. In use, the emergence profiler 50 and its core component 10 are removed together, as a unit, from the implant 20, the longer core abutment 60 is non-rotatively attached to the implant with the coping screw 64, and a second premolar-type emergence profiler guide 50' intended for use as an impression coping component, which may be identical to the first premolar-type emergence profiler 50, is fitted over the core abutment 60 engaging the ribs 62 while oriented identically to the emergence profiler 50. This assembly 50'–60 can then function as a pick-up impression coping in know fashion. The protruding supergingival end of the core component 60, together with the portion of the impression coping 50' which extends above the gum 44, will serve to retain the coping in the impression material (not shown). The coping screw 64 will extend through the impression tray (not shown) where it can be accessed to separate the impression coping assembly 50'–60 from the implant, allowing the coping assembly to be "picked-up", or retained within the impression for use in making a model of the site.

Additional means to retain the pick-up coping assembly in impression material may be provided, in the form of an annular groove 66 on the core abutment 60, as is shown in FIG. 8, for example. In this embodiment, the groove 66 is preferably located closely above the top surface of the impression coping component 50', where impression material that flows into the groove can serve to lock the coping component 50' in place on the core abutment. Another alternative is to employ the shorter abutment 10 with a wide-headed impression-coping screw 70 as illustrated in FIG. 9 and shown in U.S. Pat. No. 4,955,811 owned by the assignee of this application. In this embodiment the impression coping assembly 50'–70 that results is a transfer type coping, not a pick-up type coping.

It is noteworthy that the emergence profiler 50 can be used as an impression coping component 50' for both impression coping methods (pick-up type or transfer type). FIG. 9 illustrates the use of a wide-headed impression coping screw 70 used in conjunction with the coping component 50' and the core abutment 10. As stated previously, this configuration is used for transfer type impression coping. However, the core abutment 10 can also receive a pick-up type coping screw 64 as depicted in FIGS. 6 and 7. Further, the longer core abutment 60 shown in FIGS. 6 and 7 may also be used with both types of coping screws. FIG. 7 illustrates the use of the longer core abutment 60 with the pick-up type coping screw 64. The wide-headed transfer type coping screw 70 may also be used with the core abutment 60 provided the screw is sufficiently long to engage the internally threaded bore of the implant 20. By allowing interchangeability of coping screws with a single coping component, this invention permits one coping component to be used for either impression method. This result was not possible with prior coping components.

Figure 10:
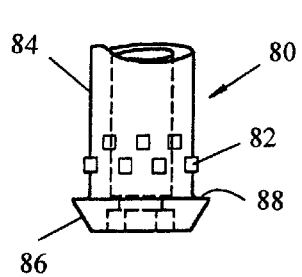
FIG. 10 is a side view of another core component.
Figure 11:
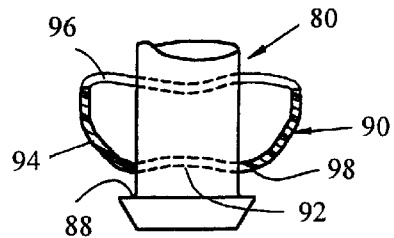
FIG. 11 is a section through another embodiment of the emergence profiler.

FIGS. 10 and 11 illustrate another embodiment of the invention employing a hollow-shell form 94 to make the emergence profiler guide member 90 of the invention. The shell form can be, for example, blow-molded of a plastics material with an outer shape and contour to mimic a natural tooth. The shell has a round hole 92 in its bottom 98 through which a core component 80 can pass. Like the bore 52 in FIG. 4, this hole 92 has a diameter sized to fit closely around the core component. In use the shell 94 is fitted onto the core component 80 with its bottom 98 seated on the shoulder 88 on the subgingival end 86 and the shell is then filled, preferably to its rim 96, around the tubular part of the core component, with a flowable filling material such as an acrylic (not shown) intended for dental use, which hardens to form a substantially solid body within the shell, thereby providing a substantially solid emergence profiler guide. The use of a flowable filling material allows the core component 80 to have multi-dimensional locking means such as projections 82 on its outer surface 84. Except for this unique difference the core component may be identical to the core components 10 or 60.

The invention shown in FIGS. 1–11 provides a new, accurate and inexpensive method and means for making and using an impression coping that faithfully reproduces the emergence profile established in the gingiva by the healing abutment component. Further, this invention can faithfully and accurately transfer the emergence profile information to a working model used to build an anatomically-shaped artificial tooth on a round-shaped implant.

Further, the invention of FIGS. 1–11 lends itself to the provision of temporary dentition. For example, the emergence profiler 50 can also function as a temporary tooth, albeit one lacking an occlusal surface. If an occlusal surface is desired the clinician can provide one by adding temporary tooth material (e.g: acrylic) to the top surface of the emergence profiler 50.

Figure 12A:
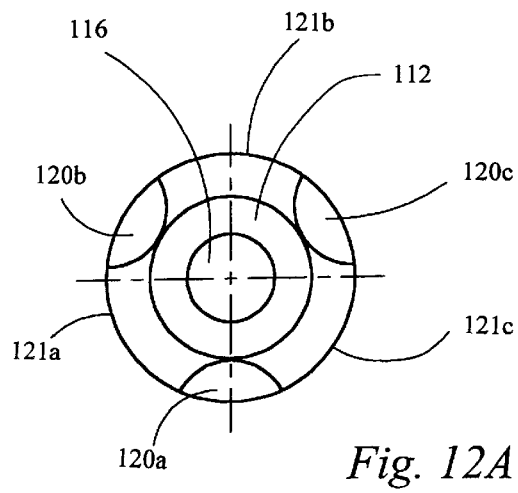
FIG. 12A is a top view of FIG. 12.
Figure 12:
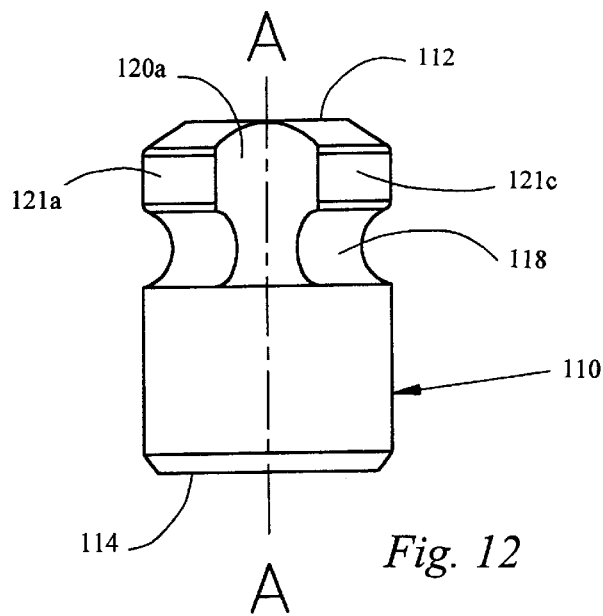
FIG. 12 is a side view of an impression coping according to the invention.
Figure 12B:
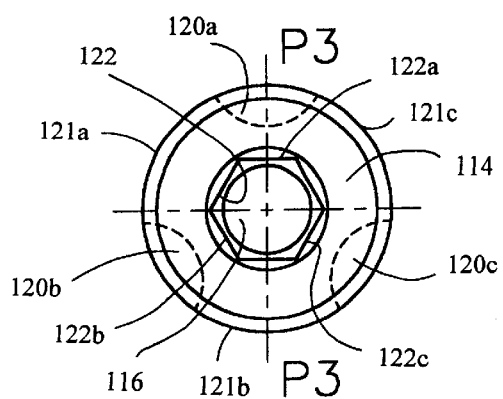
FIG. 12B is a bottom view of FIG. 12.

Referring generally to FIGS. 12–15A, inclusive, an impression coping component 110 is illustrated. The coping component 110 has a top end 112 and a bottom end 114, and a through passage 116 from one end 112 to the other 114. FIG. 12A is a view of the top end 112. FIG. 12B is a view of the bottom end 114. The coping component 110 is tubular in form, symmetrical around its longitudinal axis A-A. A portion 118 of the outer surface of the coping 110 is circumferentially recessed. Three longitudinal recesses 120a, 120b and 120c are symmetrically arrayed around the upper portion of the coping, extending from the circumferentially recess 118 to the upper end 112. The recesses 118, 120a, 120b and 120c are all formed on a circular locus, but that is by way of example only. Recesses having other transverse-sectional shapes, such as rectangular and triangular, may also be used in copings of the invention. A hexagonal anti-rotation socket 122 of known form is located in the bottom end 114, symmetrical around the axis A-A. The through passage 116 opens into this hexagonal socket.

A coping screw 124 (FIG. 14) has a shaft 126 sized to fit (preferably snugly) in the through passage 116, a threaded end 128 for engaging in a threaded bore 144 in an implant 140 (FIG. 15A), and a head 130 for manipulating the screw, and for other uses to be presently described. As is shown in FIG. 15, the head 130 abuts the end 112 of the coping component when the latter is fixed to the implant 140, which has a hexagonal boss 142 of known form to engage the socket 122. The coping screw 124 of FIG. 14 is intended to be used in transfer type impression coping applications. If a pick-up type impression application is desired, the coping screw 124a of FIG. 14A may be used. The head 130a of the pick-up type coping screw 124a is extended in length such that the top of the coping screw is positioned substantially above the top of the coping component 110. This arrangement allows the coping screw 124a to be removed from the coping component 110 after an impression has been taken, thereby allowing the component 110 to remain within the impression material as it is removed from the patient's mouth.

Figure 16:
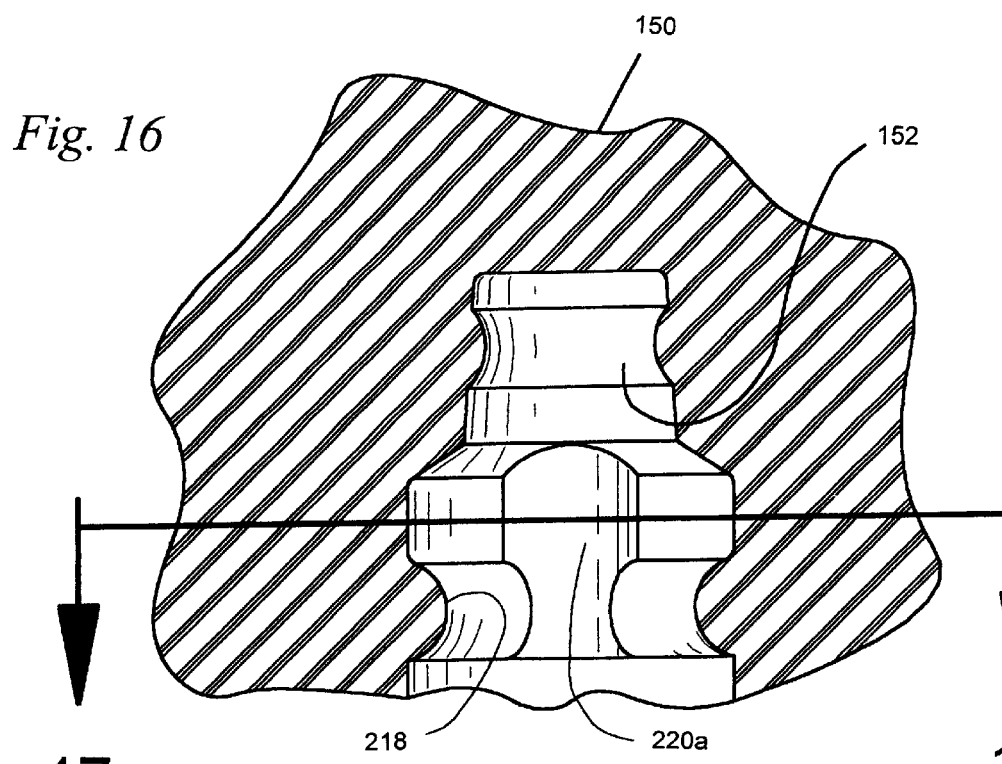
FIG. 16 is a section through impression material showing a socket formed by the coping of the invention.
Figure 17:
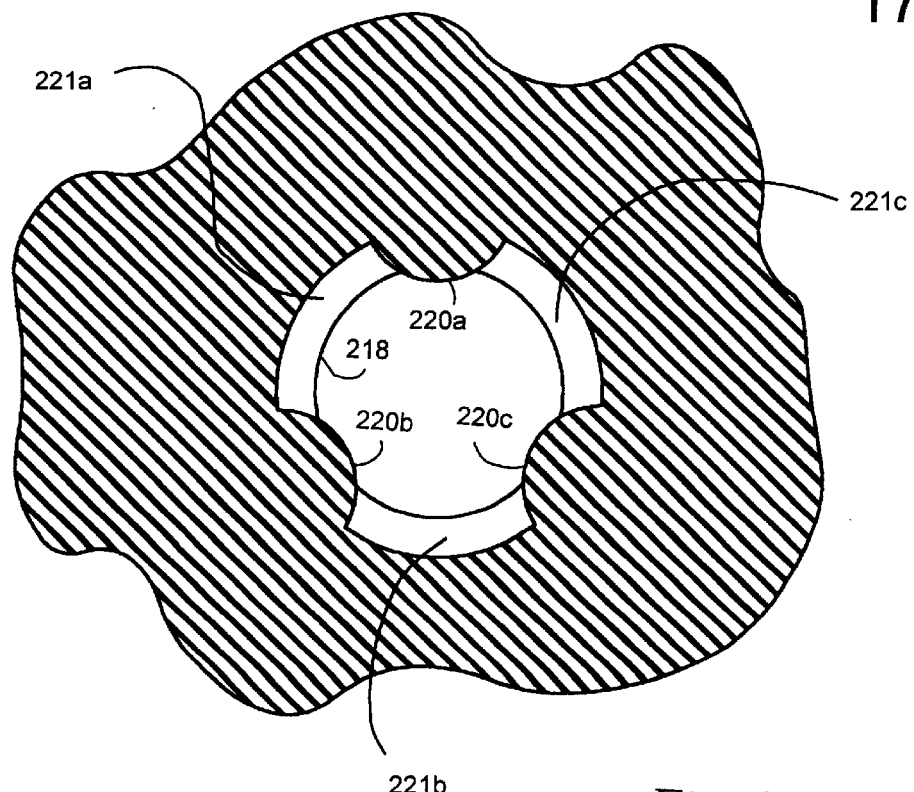
FIG. 17 is a sectional view of FIG. 16 taken on line 17—17.

The recesses 118, 120a, 120b and 120c form three projections 121a, 121b and 121c arrayed symmetrically around the axis A-A which serve as individual impression interlocking elements in impression material, shown in FIGS. 16 and 17. The socket 122 embraces a plane P1-P1 (FIG. 13). The projections 121a, 121b and 121c embrace a plane P2-P2 (FIG. 13). These planes are transverse to the axis A-A, and are spaced apart along that axis. Each of the longitudinal recesses 120a, 120b and 120c is aligned longitudinally with a specific one of the flat surfaces 122a, 122b or 122c of the hexagonal socket 122, in a plane that is parallel to the axis A-A. This is shown in FIG. 12B where plane P3-P3 is the alignment reference for recess 120a and flat surface 122a; this shows also that the recess 120a is thereby aligned also with the opposite flat surface of the socket 122. The projection 121b opposite the recess 120a is therefore aligned with the same flat surfaces of the socket as is the recess 120a. The same is true for the projection 121a opposite recess 120c, and for the projection 121c opposite recess 120b. Looking at FIG. 12B, it is apparent that this Figure can be rotated 120 degrees in either direction around the longitudinal axis A-A and the posture of the hexagonal shape of the socket 122 around the axis will remain unchanged. The impression interlocking elements 120a, 120b and 120c and the anti-rotation socket 122 are indexed for symmetry around the axis A-A.

At the time of this invention, the description above provides the optimal configuration of the coping component which employs three impression interlocking elements in cooperation with the customary hexagonal implant interlocking socket. However, it is to be understood that other embodiments are possible, and are intended to be embraced within the scope of the appended claims.

When the coping component 110 and the coping screw 124 are assembled as shown in FIG. 15, they form a compact impression transfer coping assembly with additional advantages. The head 130 has a diameter D2 which is smaller than the diameter D1 of the coping component 110. This combination forms a socket 152 in the impression material (FIGS. 16 and 17) which is narrower at its interior end that it is at its open end. During reinsertion of the coping into the impression socket the head 130 can "feel" the entrance to the narrow end and guide the coping into the socket while the impression interlocking elements 121a, 121b and 121c are being manipulated around the axis A-A.

Referring now to FIGS. 16 and 17, when the impression material sets up around the coping component 110 and coping screw head 130, an impression socket 152 is formed replicating in reverse the shape and size of the coping 110 and the screw head 130. Thus, for the annular recess 118 there is an annular bulge 218, for each longitudinal recess 120a, 120b and 120c there is a longitudinal bulge 220a, 220b and 220c, and for each projection 121a, 221b and 221c there is a corresponding recess 221a, 221b and 221c. Whenever the coping is reinserted into the socket 152, each of the projections can occupy any of the corresponding recesses, thus replicating the three possible orientation positions of the coping described above with reference to FIG. 12B.

The head 130 may take many forms. It may include a circumferential recess 132 as shown, for additional retention in the impression socket 152. It may omit any such recess. It may be shorter or longer than the head that is illustrated. It may have means to engage a driver for turning it. If the bore 116 is fitted with an internal shoulder (not shown) the shaft 126 may be altered to engage that shoulder, in which case the diameter of the head 130 may be reduced to the same as or less than the diameter of the shaft 126.

Therefore, the design of this coping component 110 further provides the advantage of enabling the use of a single coping component 110 for either transfer impression coping or pick-up impression coping applications. The coping 110 is designed to accept either a coping screw 124 with a short head 130 (as depicted in FIG. 14) or a coping screw 124a with an extended head 130a (as depicted in FIG. 14A). Since a single coping component may be used for either impression coping method, a clinician is now able to easily select the most appropriate impression coping method for a given case. A clinician need only interchange the coping screw used with the coping component in order to change techniques. Moreover, this new design feature requires only one coping component to be manufactured and inventoried contrary to the manufacture and inventory of two separate coping components in the past (one for pick-up type applications and one for transfer type applications). Therefore, this invention provides for a more modular design that is more economical for clinicians and manufacturers since only one type of coping component needs to be manufactured, purchased, and inventoried.

The coping 110 and head 130 may take a somewhat conical or pyramidal form, which has an advantage when taking an impression of a case having two copings on divergent axes. In such a case, if the two copings are cylindrical they will have remote surfaces that diverge, making it difficult to remove the copings from an impression. The conical form made possible in the present invention prevents divergence of the remote surfaces over a wide range of divergent axes.

Owing to its self-indexing and self-guiding features, the impression coping component can be made in sizes that are unusually short. For example, the distance between the top end 112 and the bottom end 114 can be as small as about 5 mm. As is mentioned above, the dimensions of the screw head 130 can be varied over a wide range without losing its self-guiding property; if that property is built into the coping component 110 the screw head 130 can be further diminished in size. Accordingly, in the claims that follow, the term "coping" is intended to encompass any structure or combination of structures that forms the impression socket 152, a unitary (one-piece) coping as well as a coping which includes a separate head such as the illustrated head 130.

The plurality of individual impression interlocking elements of the invention may be used in combination with a wrench 160 illustrated in FIGS. 18 and 18A to drive a threaded implant into a suitable prepared bore in a patient's jawbone. The coping 110 is, for example, attached to an implant 140, as is suggested in FIGS. 15 and 15A. An implant with the coping and its screw 124 attached can be delivered to a clinician in a sterile package (not shown), or the clinician can attach the coping and its screw to an implant for use initially as an implant carrier. The wrench 160 comprises a tubular body having in its interior bore 164 a plurality of longitudinal bulges 160a, 160b and 160c, corresponding, respectively, to the bulges 220a, 220b and 220c in the impression socket 152 in FIG. 17. Between these bulges are three recesses 161a, 161b and 161c, corresponding, respectively, to the recesses 221a, 221b and 221c in FIG. 17. The tubular portion of the body 162 containing these bulges and recesses fits matingly over the portion of the coping 110 which has the longitudinal recesses 120a, 120b and 120c and the projections 121a, 121b and 121c, so that the bulges of the wrench fit one each into the recesses of the coping, and the recesses 161a, 161b and 161c of the wrench fit one each over the projections 121a, 121b and 121c of the coping, thus interlocking the wrench and the coping against relative rotation around their common axis B-B. Further into the hollow bore 164 the wrench has an annular groove 166 fitted with an O-ring 168 of resilient material such as rubber or plastic. Fitted to the exterior of the wrench, a distance axially away from the tubular body 162, is a six-sided (hex) head 170, of a kind useful for turning the wrench around its axis B-B.

In use, as is shown in FIG. 19, the wrench fits over the coping component 110 and the screw head 130. The annular groove 132 is releasably grasped within the O-ring 168, which retains the coping in the wrench. Via the hex head 170 the wrench, and with it the coping 110, can be turned around the axis B-B. If the coping is attached to an implant the implant can thereby be turned into a surgically-prepared bore in the jawbone of a patient. A positive non-slipping lock against relative rotation around the axis B-B is established by the plural independent locking elements of the coping and the wrench, respectively, which is not found in the prior art. For example, in U. S. Pat. No. 5,312,254 it is proposed to use a wrench having a socket with a single flat land surface to engage and turn a coping of the kind shown in U.S. Pat. No. 4,955,811. For the same reasons that the coping component previously described provides superior indexing in a socket formed by it in impression material, the wrench and coping combination herein disclosed provides superior interlocking for wrenching purposes. With this combination, an implant can be brought to the above-mentioned bore, started and screwed into it in a continuous uninterrupted procedure. There is no need to carry the implant to the site with a first implement and thereafter complete the installation with another implement, as is taught in the '254 patent.

While the present invention has been described with reference to one or more preferred embodiments, those skilled in the art will recognize that many changes may be made thereto without departing from the spirit and scope of the present invention which is set forth in the following claims.

What is claimed is:

1. A transfer-type impression coping for cooperating with a resilient impression material to take an impression for making a model of a region in a mouth adjacent to an aperture in gingiva which exposes an implant that is installed in bone, said transfer-type impression coping comprising:

a plurality of surfaces defining a polygonal fitting for mating with a corresponding fitting of said implant;

an outer surface having a transgingival section configured to fit within said aperture and a supragingival section for embedment in said resilient impression material, said supragingival section having at least one part with a non-circular cross-sectional profile that is circumferentially symmetric around a central axis of said coping, said cross-sectional profile being configured relative to said plurality of surfaces such that an orientation of said plurality of surfaces relative to said impression material is substantially the same when it is transferred back into said impression material after said impression is taken, said transfer type impression coping capable of being transferred back into said impression material in at least two orientations after said impression is taken; and an inner surface defining a passage that is generally aligned with said implant for receiving a screw intended for fastening said impression coping to said implant.

2. The transfer-type impression coping of claim 1 wherein said inner surface and said outer surface are separated by a unitary component.

3. The transfer-type impression coping of claim 1 wherein said outer surface includes a plurality of recesses.

4. A transfer-type impression coping which is attachable to a dental implant installed into bone and which includes a polygonal boss, said coping useful in cooperation with a resilient impression material to take an impression in a mouth, said transfer-type coping comprising:

a generally tubular body having an outer surface and a longitudinal axis to be generally aligned with said implant;

a polygonal socket with "n" sides located near one end of said body for engaging said polygonal boss of said dental implant, said polygonal boss and socket for preventing relative rotation between said coping and said dental implant; and a number "m" of impression interlocking elements on said outer surface of said body, said impression interlocking elements being arranged symmetrically around said longitudinal axis of said body, said number "m" being any number greater than 1 and wholly divisible into "n."

5. The transfer-type impression coping according to claim 4, wherein n=6 and m=3.

6. The transfer-type impression coping according to claim 4, wherein said polygonal socket includes six substantially identical flat surfaces forming a hexagon.

7. The transfer-type impression coping according to claim 4, wherein each of said impression interlocking elements is formed by a generally curvilinear recess in said outer surface of said body.

8. The transfer-type impression coping according to claim 4 wherein said number "m" is 3 and said impression interlocking elements are circumferentially spaced 120° from each other around said longitudinal axis.

9. The transfer-type impression coping according to claim 8, wherein each of said impression interlocking elements is circumferentially aligned with one of said sides of said polygonal socket.

10. The transfer-type impression coping according to claim 8, wherein each of said impression interlocking elements is circumferentially aligned with one of said sides of said polygonal socket.

11. The transfer-type impression coping according to claim 8, wherein said generally tubular body includes a circumferential recess that intersects with each of said impression interlocking elements.

12. The transfer-type impression coping according to claim 8, wherein each of said impression interlocking elements is formed by a flat surface on said outer surface of said body.

13. A transfer-type coping attachable on a common axis to a dental implant including a first polygonal fitting, said transfer-type impression coping useful in cooperation with a resilient impression material to take an impression in a mouth, said transfer-type coping comprising:

a generally tubular body having a longitudinal axis, an outer surface, and a through-bore for receiving a screw;

a second polygonal fitting located near one end of said body for engaging said first polygonal fitting of said dental implant for preventing relative rotation between said coping and said dental implant;

at least two impression interlocking elements formed on said outer surface for engaging said impression material, said impression interlocking elements being circumferentially symmetric around said longitudinal axis for creating a symmetrical opening in said impression material into which said transfer-type impression coping can be reinserted in at least two distinct orientations.

14. The transfer-type impression coping according to claim 13, wherein said second polygonal fitting has a hexagonal shape and said impression interlocking elements are three in number.

15. The transfer-type impression coping according to claim 14, wherein each of said three impression interlocking elements is aligned with a corresponding one flat surface on said polygonal fitting.

16. The transfer-type impression coping according to claim 13, wherein said impression interlocking elements are formed by a recess in said outer surface.

17. The transfer-type impression coping according to claim 16, wherein said recess is curvilinear when viewed in cross section.

18. The transfer-type impression coping according to claim 16, wherein said recess includes a flat surface when viewed in cross section.

19. The transfer-type impression coping according to claim 13, wherein said generally tubular body includes a circumferential recess that intersects with each of said impression interlocking elements.

20. A method for creating a model of a mouth having a dental implant that is installed therein and includes a first polygonal fitting, said method comprising:

installing an impression coping on said implant, said impression coping including a second polygonal fitting mating with said first polygonal fitting and at least two impression interlocking elements being arranged circumferentially symmetrical around a longitudinal axis of said impression coping;

applying impression material into said mouth and around said at least two impression interlocking elements of said coping, said second polygonal fitting having a predetermined angular orientation with respect to said impression material after being applied around said coping;

removing said impression material from said mouth;

removing said impression coping from said implant independent of said step of removing said impression material from said mouth;

reinserting said impression coping into an opening within said impression material in one of at least two available orientations, said predetermined angular orientation of said second polygonal fitting and said impression material being substantially reestablished upon reinsertion.

21. The method of claim 20, wherein said second polygonal fitting has a hexagonal shape and said impression interlocking elements are three in number.

22. The method of claim 21, wherein each of said three impression interlocking elements is aligned with a corresponding one flat surface on said polygonal fitting.

23. The method of claim 20, wherein said step of reinserting including the step of registering said impression coping axially in said opening via use of circumferential recess in said impression coping.

24. The method of claim 20, wherein each of said impression interlocking elements are formed by a recess in said outer surface, said recess is curvilinear when viewed in cross section.

25. The method of claim 20, wherein each of said impression interlocking elements are formed by a recess in said outer surface, said recess includes a flat surface when viewed in cross section.

26. The transfer-type impression coping of claim 1, further in combination with said implant.

27. A combination of an implant having a polygonal boss and a transfer-type impression coping attachable to said dental implant and useful in cooperation with impression material to take an impression in a mouth, said transfer-type coping including:

a generally tubular body;

a polygonal socket with "n" sides for engaging said polygonal boss of said dental implant, said polygonal boss and socket preventing relative rotation between said coping and said dental implant; and a number "m" of impression interlocking elements being arranged symmetrically around said longitudinal axis of said body, said number "m" being any number greater than 1 and wholly divisible into "n."

28. The combination according to claim 27, wherein n=6 and m=3.

29. The combination according to claim 27, wherein said number "m" is 3 and said impression interlocking elements are circumferentially spaced 120° from each other around said longitudinal axis.

30. A transfer-type impression coping, comprising:

an outer surface to be embedded in resilient impression material, said outer surface having a non-circular cross-sectional profile, said non-circular cross-sectional profile being circumferentially symmetric around a central axis of said coping such that said transfer type impression coping can be reinserted into said impression material in at least two orientations after an impression is taken.

31. The transfer-type impression coping of claim 30, further including means for registering the axial position of said impression coping within said impression material.

32. The transfer-type impression coping of claim 31, wherein said means is a circumferentially extending recess in said coping.

33. The transfer-type impression coping of claim 31, wherein said means is a circumferentially extending recess in a head of a screw for holding said impression coping on an implant.

* * * * *

UNITED STATES PATENT AND TRADEMARK OFFICE
CERTIFICATE OF CORRECTION

PATENT NO. : 6,290,499 B1
DATED : September 18, 2001
INVENTOR(S) : Lazzara et al.

It is certified that error appears in the above-identified patent and that said Letters Patent is hereby corrected as shown below:

<u>Title page,</u>
Item [56], OTHER PUBLICATIONS, after "DIA™ Dental Imaging Associates", delete "Inplamed" and insert -- Implamed --

<u>Column 9,</u>
Lines 47, 51 and 55, delete "8" and insert -- 4 --.

Signed and Sealed this

Twenty-fifth Day of June, 2002

Attest:

Attesting Officer

JAMES E. ROGAN
*Director of the United States Patent and Trademark Office*